United States Patent [19]
Büchi et al.

[11] 3,931,323
[45] Jan. 6, 1976

[54] PROCESS FOR THE PREPARATION OF ALKENOYL-SUBSTITUTED CYCLOHEXENES

[75] Inventors: George Hermann Büchi; John Christopher Vederas, both of Cambridge, Mass.

[73] Assignee: Firmenich SA, Geneva, Switzerland

[22] Filed: Mar. 21, 1973

[21] Appl. No.: 343,490

[30] Foreign Application Priority Data

Mar. 30, 1972 Switzerland ........................ 4769/72

[52] U.S. Cl. ............... 260/586 R; 131/17; 252/522; 260/307 H; 260/348 R; 260/563 R; 260/566 R; 260/566 A; 426/155; 426/175

[51] Int. Cl.[2] ........................................ C07C 45/00

[58] Field of Search ......... 260/586 R, 587, 570.5 C, 260/307 H, 563 R, 566 R, 566 A

[56] References Cited

OTHER PUBLICATIONS

Elderfield, "Heterocyclic Comp.," Vol. 5, p. 464 (1957).

Weygand et al., "Prep. Org. Chem.," pp. 80, 81, (1972).

*Primary Examiner*—Norman Morgenstern
*Attorney, Agent, or Firm*—Pennie & Edmonds

[57] ABSTRACT

New heterocyclic derivatives containing nitrogen useful for perfumery and the flavour industry and use of same as perfuming and/or flavouring ingredients in the manufacture of perfumes and perfumed products and/or in the preparation of artificial flavours for foodstuffs, beverages, animal feeds, pharmaceutical preparations and tobacco products.

Process for preparing the said heterocyclic derivatives which are equally useful as starting materials for preparing known fragrance compounds.

2 Claims, No Drawings

PROCESS FOR THE PREPARATION OF ALKENOYL-SUBSTITUTED CYCLOHEXENES

SUMMARY OF THE INVENTION

This invention relates to new nitrogen heterocyclic derivatives having the formula

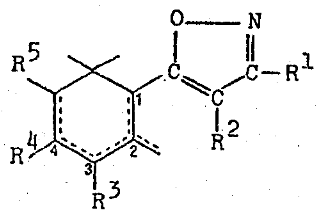

I wherein:

the ring contains one endocyclic double bond in position 1, 2, 3 or 4, or an exocyclic double bond in position 2, or two conjugated double bonds in positions 1 and 3, the double bonds being represented by the dotted lines; and each of the symbols $R^1$, $R^2$, $R^3$, $R^4$ and $R^5$ represents either a lower alkyl containing from 1 to 6 carbon atoms, or a hydrogen atom.

The present invention relates further to a process for preparing the compounds of formula I, as well as to the use of same as perfuming and flavouring ingredients in accordance with a compounding technique conventional in the art.

The present invention relates further to new β-amino-ketones of formula

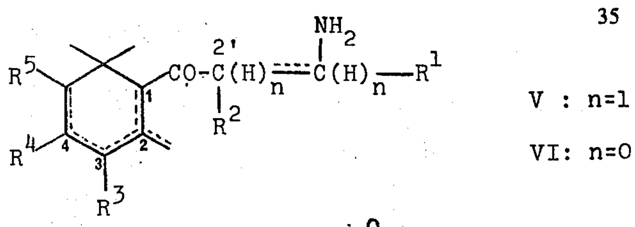

V : n=1

VI: n=0 wherein:

$n$= zero or 1;

the side-chain attached at position 1 of the ring contains one double bond (when $n$ = zero) or one single bond (when $n$ = 1) in position 2';

the ring contains one or two double bonds as aforesaid; and the symbols $R^1$, $R^2$, $R^3$, $R^4$ and $R^5$ have the same meaning as that indicated for formula I.

BACKGROUND OF THE INVENTION

The compounds of formula I belong to a new class of chemical compounds which have the characteristic structure of 1,2-oxazole or isoxazole

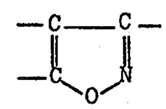

The synthesis of isoxazolic derivatives was thoroughly studied in the past and several methods for preparing the said compounds are known and described in the scientific literature [cf. e.g.: Ber., 28,2540 (1895); idem. 36, 3665 (1903); Compt. rend., 137, 795 (1903); J. Am. Chem. Soc., 49, 2078 (1927); Gazz. Chim. Ital., 70, 676 (1940); idem, 72, 99 (1942); idem, 76, 148 (1946)]. The methods described in the aforementioned references can be distinguished depending on whether they relate to: syntheses achieved by 1. reacting 1,3-dicarbonyl compounds with hydroxylamine in accordance with the following scheme:

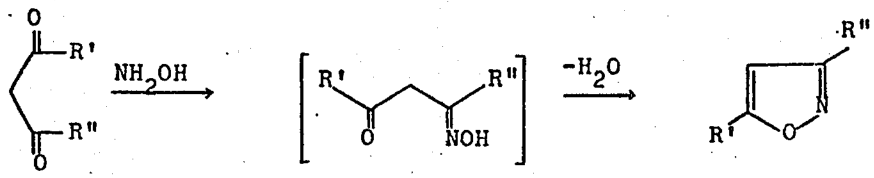

2. reacting α-acetylenic ketones or aldehydes with hydroxylamine in accordance with the following scheme:

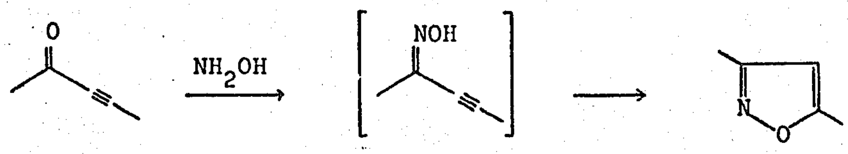

3. reacting halogenated α, β-ethylenic ketones or aldehydes with hydroxylamine according to

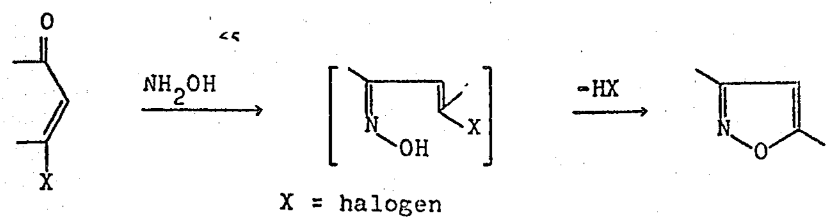

X = halogen or 4. reacting $\alpha,\beta$-unsaturated ketones with hydroxylamine

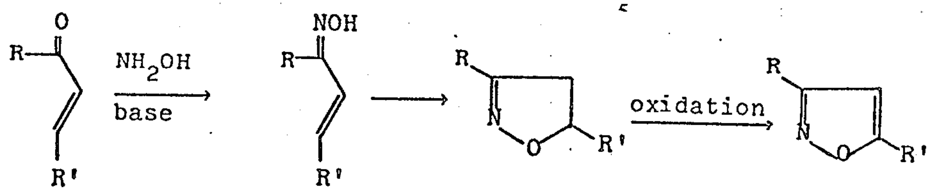

In accordance with this latter method an intermediate isoxazoline is obtained which, when subjected to an oxidation, e.g. by means of chromic acid, can be converted into the corresponding isoxazole derivative. This latter synthesis has however the disadvantage of yielding several by-products depending on the acidity of the reaction medium, the respective proportions of the reagents used and the nature of the substituents.

PREFERRED EMBODIMENTS OF THE INVENTION

We have now unexpectedly found that by reacting a compound of formula

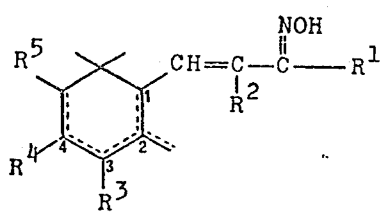

wherein the dotted lines as well as the symbols $R^1$, $R^2$, $R^3$, $R^4$ and $R^5$ have the same meaning as aforeindicated, with a halogen, e.g. iodine or bromine, or with a donor of positive halogen, e.g. N-bromosuccinimide, preferably in a neutral or alkaline medium, isoxazoles having formula I are obtained.

The process of the invention has the advantage, as compared with the known process described in particular sub 4 above, of directly yielding an isoxazole without forming the intermediate isoxazoline. Thus, one operational step is omitted and thereby the necessity of proceeding to an oxidation which, in many cases, cannot be performed (e.g. when a molecule possesses further oxidizable groups), is avoided.

Nitrogen derivatives II, used as starting materials in the process of the invention, can be prepared by reacting $\alpha,\beta$-unsaturated ketones of formula

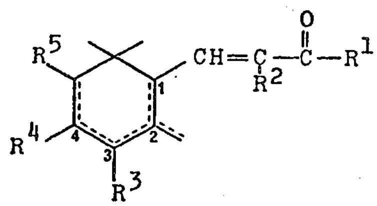

(wherein the substituents $R^1$, $R^2$, $R^3$, $R^4$ and $R^5$ and the dotted lines are defined as aforesaid) with hydroxylamine, generally in the form of its hydrochloride, according to the conventional techniques (cf. in this respect: L.F. Fieser and M. Fieser, Organic Chemistry, Reinhold Publ. Corp., New York, (1956), p. 211 ff.)

The ketones of formula III represent a class of derivatives which are better known under the name of ionones and whose preparation has been thoroughly studied and described, viz. in Helv. Chim. Acta, 30, 2213 (1947); idem, 30,2216 (1947); Fortschritte der Chemie organischer Naturstoffe, VIII, 146 (1951); J. Chem. Soc., 1074 (1951); J. Org. Chem., 32, 180 (1967). Some of the said compounds of formula III are commercially available.

The formation of isoxazoles I according to the invention is preferably effected by means of iodine. This latter is maintained, at least partially, in solution in an aqueous medium by the addition of an alakli metal iodide, e.g. potassium iodide.

The cyclization reaction is preferably performed in an aqueous medium in the presence of an inert organic solvent such as an alcohol, e.g. methanol, ethanol, n-propanol or isopropanol, or in the presence of an ether, e.g. ethyl ether, dioxan, tetrahydrofuran, monoglyme or diglyme. Methyl alcohol or tetrahydrofuran are preferred.

The said cyclization may occur in a wide temperature range. The formation of the desired isoxazole was observed at temperatures from 25° to 50°C. However, it is preferred to operate at temperatures higher than those aforeindicated. Indeed, it has been found that the best yields of final product were obtained when the cyclization was effected at the boiling temperature of the chosen solvent or at a temperature in the vicinity thereof. Of course, higher temperatures can also be used, in particular when the operation is carried out at a pressure exceeding the atmospheric pressure.

The reaction time can also vary within a wide range. Thus, if the reaction is carried out at a temperature from about 60° to about 80°C, good yields of final product are obtained within a reaction time comprised between about 1 hour and about 24 hours. Generally 2½ hours are sufficient for the complete conversion of compounds II into their cyclic derivatives. As mentioned above, the reaction is preferably carried out in a neutral or alkaline medium. pH values comprised between about 7 and about 12 can be conveniently used. In order to attain and to maintain in the course of the reaction this preferred acidity a buffer can be used, e.g. a boric or phosphoric salt of an alkali metal, e.g. sodium tetraborate, or sodium or potassium mono- or dihydrogenophosphate, or sodium hydrogenocarbonate. For reasons of economy the last mentioned buffer reagent is preferred.

When iodine is used as the cyclizing agent, the reaction is preferably carried out in the absence of light; however, this condition is not essential.

According to another process of the present invention, isoxazoles I are prepared by cyclizing the epoxidized derivatives on the side chain of compounds II. More particularly, by cyclizing a compound of formula

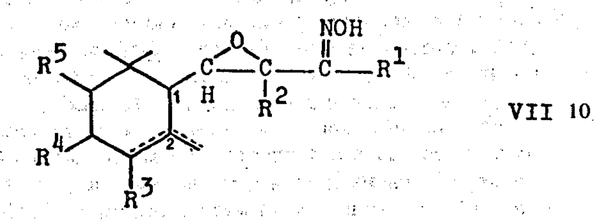

containing an exocyclic or endocyclic double bond in position 2 of the ring in the presence of a dehydrating agent, which is preferably acid, the corresponding isoxazoles are obtained in a very good yield.

The compounds of formula VII can be readily obtained from the corresponding $\alpha$, $\beta$-epoxidized ketones by reacting these latter with hydroxylamine in accordance with the conventional techniques (cf. e.g. : L. F. Fieser and M. Fieser, Organic Chemistry, Reinhold Publ. Co., New York (1956), p. 211 and ff).

The $\alpha$, $\beta$-epoxidized ketones used as starting materials in the aforesaid process can be prepared according to the method described, e.g., in Helv. Chim. Acta, 53, 531 (1970).

Preferred acidic dehydrating agents include strong organic and mineral acids, such as p-toluenesulphonic acid, sulphuric acid or hydrochloric acid.

The cyclization of epoxy-oximes VII can be carried out by dissolving the starting material in an inert solvent. Suitable solvents include aromatic hydrocarbons, e.g. benzene or toluene, or cycloaliphatic hydrocarbon, e.g. cyclohexane. The temperature used can vary widely, but the cyclization is generally performed at a temperature from about 20°C to the boiling temperature of the solvent chosen, preferably from about 60° to about 90°C.

Although the intramolecular reaction between an oxime group -NOH and an epoxy center is known and described [cf. particularly: Ber., 49, 2782 (1916)], the above described process provides a new and economic solution of the specific problem brought about by the synthesis of isoxazoles I.

Apart from being useful in their own right by virtue of their valuable organoleptic properties, the compounds of formula I are also useful as intermediates in the preparation of compounds of formula

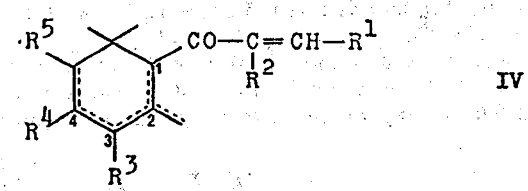

(wherein the symbols $R^1$, $R^2$, $R^3$, $R^4$ and $R^5$ and the dotted lines have the meaning already given), which are very useful as odoriferous or flavouring ingredients [cf. in this respect e.g.: French Pat. No. 1,591,031; Swiss Pat. Nos. 513,094, 513,096, 513,097; Helv. Chim. Acta, 53, 541 (1970)].

The compounds of formula I which contain an endocyclic double bond in position 2 of the ring can be converted into their corresponding derivatives containing a double bond in position 1 of the ring by means of a basic or acid agent.

The present invention relates further to a new process for the preparation of compounds of formula IV, which process comprises reducing a compound of formula I, and subsequently removing an ammonia molecule of the resulting $\beta$-amino-ketone of formula

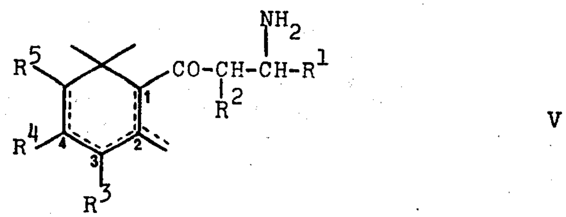

(wherein the symbols $R^1$, $R^2$, $R^3$, $R^4$ and $R^5$, and the dotted lines have the meaning already given).

The above mentioned process can be illustrated by the following reaction scheme:

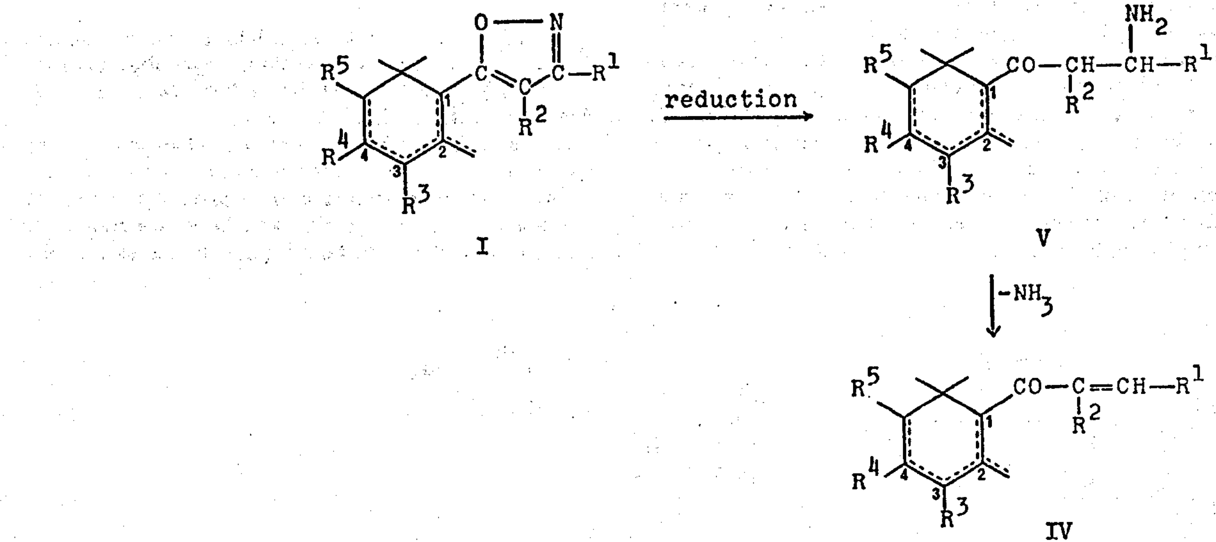

The reduction of compounds I can be effected by means of a metal such as an alkali metal, e.g. lithium, sodium or potassium, or an alkaline earth metal, e.g. calcium, in solution. The solutions are preferably prepared in liquid ammonia in the presence of a proton donating agent according to known techniques [A. J. Birch, Quart. Rev. (London), 4, 69 (1950) H. O. House, Modern Synthetic Reactions, W. A. Benjamin Inc. (1965), New York, p. 50 and ff.].

According to a modification of the aforedescribed process, the compounds of formula V can also be prepared by reducing the isoxazolium salts of formula

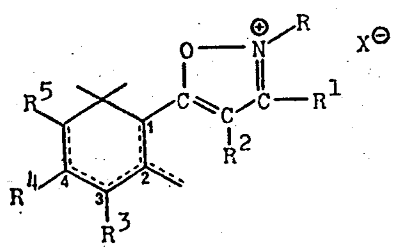

wherein R represents a lower alkyl, e.g. methyl or ethyl, and $X^-$ represents an anion, e.g. $I^-$, $Br^-$, $Cl^-$, $BF_4^-$, or $ClO_4^-$, according to the same conditions as those described above for the reduction of compounds I. The compounds of formula *Ib* can be obtained by quaternization of the osixazoles I by means of the usual techniques, e.g. by treatment with an alkyl halide. Typically, the isoxazolium iodides are prepared by heating compounds I in the presence of equivalent amounts or an excess of methyl iodide. When carrying out the quaternization there was also observed a partial isomerization of the cyclic double bond of the cyclohex-2-ene derivatives into their cyclohex-1-ene derivatives. This isomerization can be represented as follows

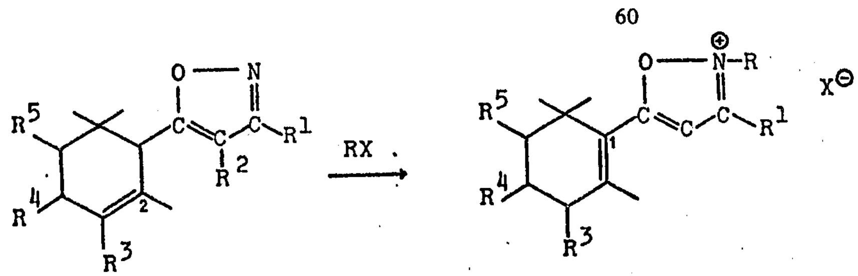

The removal of ammonia from the obtained β-aminoketone can take place by means of a mineral or organic acid or even more simply by the action of heat. Thus, good yields of final product are obtained by the use of p-toluene-sulphonic acid or by heating the β-amino-ketone at a temperature from about 80° to about 250°C. In order to facilitate the removal of ammonia, a slow stream of inert gas, e.g. argon, can be bubbled through the reaction medium subjected to heating.

Another modification of the process of the present invention consists in reducing compounds of formula I by means of a catalytic hydrogenation so as to provide an imino-ketone which by subsequent reduction, yields an amino derivative of formula V.

The reduction can be performed by means of the techniques described above for the reduction of compounds I; typically, by the so-called "Birch"-method [cf.: cited references].

The variant referred to may be illustrated by the following reaction scheme:

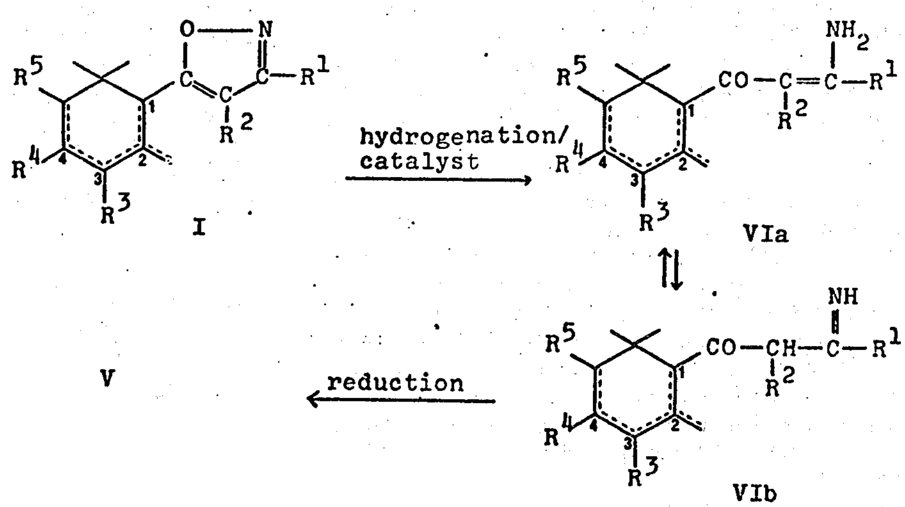

The obtained imino-ketones VIa, b can also be reduced by means of sodium cyanohydroborate ($NaBH_3CN$) according to the method described in J. Am. Chem. Soc., 93, 2897 (1971).

Owing to the combined action of the two processes of the invention it is thus possible to convert a compound having an ionone structure III into its derivative of formula IV. This conversion can be considered as a transposition of the carbonyl group in the side chain and may be illustrated schematically as follows:

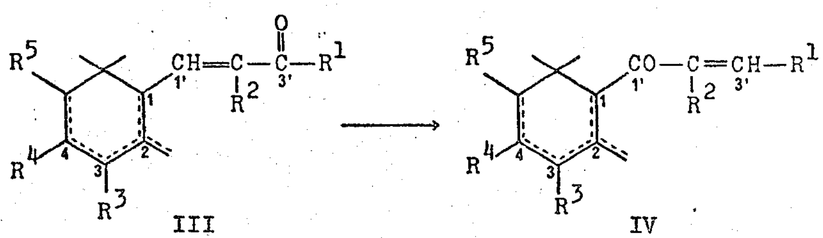

The said conversion represents a hitherto unknown and technically original solution of the problem brought up by the synthesis of unsaturated cyclic ketones IV. Most of these compounds, and various processes for their preparation have been described in the past. The synthetic methods used heretofore for the preparation of such compounds include:

a. partial hydrogenation of the corresponding acetylenic derivatives [Swiss Pat. No. 498,795];
b. direct condensation of ann organo-metallic propene derivative with a cyclogeranoyl derivative [Swiss Pat. No. 503,684];
c. cyclization of a "pseudo-ketone" by means of an acidic cyclization agent [Swiss Pat. No. 503,685];
d. dehydrogenation of a cyclohexenic ketone to obtain the corresponding cyclohexadienic derivative [Swiss Pat. No. 505,733].

The present invention provides a new process for preparing the ketones of formula IV, having the advantages of affording better yields and using more readily accessible starting materials than the earlier processes.

Typical examples of the compounds belonging to one of the aforecited formulae include:

3-Methyl-5-[2,6,6-trimethyl-cyclohex-2-en-1-yl]-isoxazole,
3-Methyl-5-[2,6,6-trimethyl-cyclohex-1-en-1-yl]-isoxazole,
3-Methyl-5-[2-methylene-6,6-dimethyl-cyclohex-1-yl]-isoxazole,
3-Methyl-5-[2,6,6-trimethyl-cyclohexa-1,3-dien-1-yl]-isoxazole,
3-Methyl-5-[2,5,6,6-tetramethyl-cyclohex-2-en-1-yl]isoxazole,
3,4-Dimethyl-5-[2,6,6-trimethyl-cyclohex-2-en-1-yl]-isoxazole,
2,6,6-Trimethyl-1-[3-amino-but-2-enoyl]-cyclohex-2-ene,
2,6,6-Trimethyl-1-[3-amino-but-2-enoyl]-cyclohex-1-ene,
2-Methylene-6,6-dimethyl-1-[3-amino-but-2-enoyl]-cyclohexane.

The compounds of formula I possess interesting organoleptic properties and impart to the substances to which they are added fruity and sweet notes reminiscent of the fragrance of certain tobaccos. They are used in particular for modifying, reinforcing or improving the olfactive properties of perfume compositions and as odoriferous ingredients in diluted or concentrated perfumes and in perfumed products.

The concentration at which isoxazoles I are used in order to produce an interesting effect vary widely.

In perfume compositions, e.g., interesting effects can be achieved by the presence of the new compounds in concentrations of 0.5 to 1% of the total weight of the perfumed composition. Depending on the organoleptic result which is to be achieved, these concentrations can be as high as 10 – 15% or even higher.

If the compounds of formula I are used for modifying, improving or reinforcing the organoleptic properties of foodstuffs, animal feeds, beverages or tobacco, they can be used at proportions of from about 10 to 100 ppm, based on the product to be flavoured.

In all cases, the ranges mentioned above may be increased beyond the indicated values.

The invention is illustrated by the following examples, in which all temperatures are expressed in degrees centigrade.

EXAMPLE 1

3-Methyl-5-[2,6,6-trimethyl-cyclohex-2-en-1-yl]-isoxazole

A solution of 88.9 g of sodium hydrogenocarbonate in 750 ml of water was added, while stirring, to a solution of 530 g α-ionone oxime (0.260 mole) in 750 ml of tetrahydrofuran.

The process was then carried on in the absence of light, and a solution of 148.6 g of potassium iodide and 69.2 g of iodine (0.270 mole) in 500 ml of water was added. After refluxing for 7 hours, the solution was allowed to stand overnight. After dilution with 500 ml of a concentrated solution of sodium bisulphite in water, the reaction mixture was extracted with ether (750 ml) and the combined organic extracts were dried over anhydrous sodium sulphate and concentrated under reduced pressure. Distillation of the thus obtained residue yielded 28.75 g of isoxazole with a yield of 54%. B.p. 69°–70°/0.04 Torr.

IR ($CHCl_3$) : 2960, 1595, 1445, 1415 $cm^{-1}$

NMR ($CDCl_3$) : 0.73 (3H, s); 0.99 (3H, s); 1.55 (3H, m); 2.22 (3H, s); 2.92 (1H, broad band, s); 5.49 (1H, m); 5.68 (1H, s); 1.2–2.2 (4H, multiplet) δ ppm UV (95% ethanol) : nm max 218 (ε 9750).

MS (70 eV) : $M^+ = 205$.

The α-ionone oxime used as starting material for the preparation of the isoxazole according to the method described above, can be prepared as follows:

77 g of hydroxylamine hydrochloride and 125 g of anhydrous sodium acetate in 200 ml of water were added to a solution of 200 g of α-ionone in 500 ml of ethanol. The reaction was slightly exothermic and the temperature rose to about 35°. After stirring of the reaction mixture for 15 minutes, the volatile portions were distilled off under reduced pressure. The residual aqueous solution was then diluted with 200 ml of water and extracted with two fractions of 150 ml each of petroleum-ether (b.p. 80°–100°). The combined organic extracts were washed with water and a 10% diluted solution of sodium hydrogenocarbonate until neutrality. The evaporation of the volatile portions resulted in a residue constituted by the desired oxime (210 g). An analytical sample was prepared by purification by means of thin layer chromatography.

EXAMPLE 2

2,6,6-Trimethyl-1-[but-2-enoyl]-cyclohex-2-ene a. 4.10 g (0.020 mole) of 3-methyl-5-[2,6,6-trimethyl-cyclohex-2-en-1-yl]-isoxazole were dissolved in 5 ml of anhydrous ethanol and the solution was added to 0.173 g of a mixture of 83.6% of platinum oxide in 30 ml of ethanol, the said mixture having previously been subjected to a hydrogenation. The solution was then subjected to a hydrogenation at room temperature and at atmospheric pressure and, after absorption of one equivalent of hydrogen, filtered through a "Celite" carrier. After having been concentrated under reduced pressure the residual solution was subjected to chromatography on a magnesium silicate column by elution with a mixture of chloroform/hexane (25/75) to yield 3.73 g (yield: 90%) of 2,6,6-trimethyl-1-[3-amino-but-2-enoyl]-cyclohex-2-ene.

IR ($CHCl_3$) : 3485, 2950, 1615, 1590, 1520 $cm^{-1}$

NMR ($CDCl_3$) : 0.89 (6H, s); 1.58 (3H, m); 1.90 (3H, s); 2.38 (1H, broad band, s); 5.06 (1H, broad band, s); 5.50 (1H, m); 1.2 – 2.3 (4H, multiplets) δ ppm UV (95% ethanol) : nm max 301 (ε 18,400)

MS (70 eV) : $M^+ = 207$.

To a mixture of liquid ammonia (500 ml), anhydrous tetrahydrofuran (100 ml), tert-butanol (14 ml) and 2.004 g (9.68 moles) of 2,6,6-trimethyl-1-[3-amino-but-3-enoyl]-cyclohex-2-ene, kept under stirring, sodium metal was added until the solution had a steady blue colour. The reaction mixture was stirred for 15 more minutes and solid ammonium chloride was then added thereto until complete discolouration. The ammonia was removed under a stream of argon. 25 ml of ether followed by 75 ml of a concentrated aqueous solution of ammonium chloride were added to the reaction mixture, and the whole was extracted with two fractions of 200 ml of ether and 100 ml of chloroform, respectively. The combined organic extracts were dried and concentrated under reduced pressure to yield 2 g of a product which, after having been refluxed in 40 ml of toluene, gave a solution which was subjected to fractional distillation and yielded 1.45 g of 2,6,6-trimethyl-1-[but-2-enoyl]-cyclohex-2-ene. The analytical data of the obtained product were identical with those of a pure sample prepared by one of the known methods.

b. To a mixture of liquid ammonia (500 ml), tetrahydrofuran (100 ml), tert-butanol (14 ml) and 3-methyl-5-[2,6,6-trimethyl-cyclohex-2-en-1-yl]-isoxazole (10.11 g; 49.3 millimoles), kept under stirring, there was added sodium metal until the solution acquired a steady blue colour. The reaction mixture was stirred for 15 more minutes and solid ammonium chloride was then added thereto until complete discolouration. The ammonia was then removed under a stream of argon. After having added 100 ml of ether and 500 ml of a concentrated ammonium chloride solution in water, the mixture was extracted with two fractions of 500 ml of ether and 250 ml of chloroform, respectively. The combined organic extracts were dried over anhydrous sodium sulphate, concentrated under reduced pressure and the thus obtained residue was dissolved in 400 ml of toluene. The said solution was then run down through a Pyrex glass column (13 mm × 150 mm) filled with glass helices previously washed with sulphuric acid and water (3/32 in), heated to 225°.

During the pyrolysis a slow stream of argon was circulated through the system and the product formed was collected in a container cooled by means of dry ice. A concentration under reduced pressure followed by a fractional distillation yielded ca. 8.0 g of 2,6,6-trimethyl-1-[but-2-enoyl]-cyclohex-2-ene (yield 82%). A further purification was carried out by chromatography on a column of magnesium silicate (250 g) by elution with a mixture of chloroform/hexane (25/75) followed by evaporation of the volatile portions and fractional distillation of the obtained residue. 2.88 g of pure ketone product were thus prepared, b.p. 55°–56°/0.04 Torr. The analytical data of the obtained product was identical with those of a pure sample prepared by one of the known methods (Swiss Pat. No. 503,685).

EXAMPLE 3

3-Methyl-5-[2,6,6-trimethyl-cyclohex-1-en-1-yl]-isoxazole

A solution of sodium hydrogenocarbonate (136 g) in 1300 ml of water was added, while stirring, to a solution of β-ionone oxime (85 g; 0.410 mole) in 1500 ml of tetrahydrofuran.

The process was then carried on in the absence of light, and a solution of potassium iodide (235 g; 1.41 moles) and iodine (109 g; 0.43 mole) in 1000 ml of water was added. After having been refluxed for 4 hours, the solution was allowed to stand overnight. After dilution with 1500 ml of a concentrated solution of sodium bisulphite in water the reaction mixture was extracted with ether (3 litres) and the combined organic extracts were dried over anhydrous sodium sulphate and concentrated under reduced pressure. The fractional distillation of the thus obtained residue yielded 77.2 g of isoxazole (yield 91%), b.p. 70°–71°/0.03 Torr.

IR ($CHCl_3$) : 2930, 1655, 1585, 1410 $cm^{-1}$

NMR ($CDCl_3$) : 1.00 (6H, s); 1.50 (3H, s); 2.27 (3H, s); 5.86 (1H, s); 1.5 - 2.2 (6H, multiplets) δ ppm UV (95% ethanol): nm max 209, 224

MS (70 eV) : $M^+ = 205$.

The β-ionone oxime used as starting material for the preparation of the isoxazole according to the method described above, can be prepared as follows:

77 g of hydroxylamine hydrochloride and 125 g of anhydrous sodium acetate in 200 ml of water were added to a solution of 200 g of β-ionone in 500 ml of ethanol. The reaction was slightly exothermic and the temperature rose to about 35°. The reaction mixture was stirred for 15 more minutes and the volatile portions were distilled off under reduced pressure. The residual aqueous solution was then diluted with 200 ml of water and extracted with two fractions of 150 ml each of petroleum-ether (b.p. 80°–100°). The combined organic extracts were washed with water and a 10% diluted solution of sodium hydrogenocarbonate until neutrality. The evaporation of the volatile portions resulted in a residue constituted by the desired oxime (210 g). An analytical sample was prepared by purification by means of thin layer chromatography. The obtained product had a b.p. of 90°/0.001 Torr.

EXAMPLE 4

2,6,6-Trimethyl-1-[but-2-enoyl]-cyclohex-1-ene a. 30.75 g (0.15 mole) of 3-methyl-5-[2,6,6-trimethyl-cyclohex-1-en-1-yl]-isoxazole were dissolved in 50 ml of dry ethanol and the solution was added to 1.396 g of a mixture of 82.9% of platinum oxide in 600 ml of ethanol, the said mixture having previously been subjected to a hydrogenation. The alcoholic solution was then subjected to a hydrogenation at ordinary temperature and pressure and, after absorption of one equivalent of hydrogen, was filtered through a "Celite" carrier. After having been concentrated under reduced pressure, the residual mixture was recrystallized from hexene containing traces of ethanol to yield 30.91 g (yield 100%) of 2,6,6-trimethyl-1-[3-amino-but-2-enoyl]-cyclohex-1-ene which exists in two interconvertible crystalline structures: m.p. 124.5°–125.0° and 135°–136°.

IR ($CHCl_3$) : 3490, 1610, 1510 $cm^{-1}$

NMR ($CDCl_3$) : 1.09 (6H, s); 1.56 (3H, s); 1.92 (3H, s); 5.00 (1H, broad band, s); 1.4 -2.1 (6H, multiplets) δ ppm UV (95% ethanol): nm max 303 (ε 20,100)

MS (70 eV) : $M^+ = 207$.

To a mixture of liquid ammonia (250 ml), anhydrous tetrahydrofuran (15 ml), tert-butanol (0.358 g) and 1.002 g (4.84 millimoles) of 2,6,6-trimethyl-1-[3-amino-but-3-enoyl]-cyclohex-1-ene, kept under stirring, there was added sodium metal until the solution acquired a steady blue colour. The reaction mixture was stirred for 15 more minutes and solid ammonium chloride was added thereto until complete discolouration and the ammonia was then evaporated under a stream of argon. After having added to the mixture 25 ml of ether and 75 ml of a concentrated ammonium chloride solution in water, the mixture was extracted with two fractions of 200 ml of ether and 100 ml of chloroform, respectively. The combined organic extracts were dried over anhydrous sodium sulphate, concentrated under reduced pressure and the thus obtained residue (1.038 g) was dissolved in 10 ml of toluene. The said solution was then refluxed overnight, then concentrated under reduced pressure. The thus obtained residue was subjected to a fractional distillation to yield 0.177 g of 2,6,6-trimethyl-1-[but-2-enoyl]-cyclohex-1-ene. The analytical data of the obtained product were identical with those of a pure sample prepared by one of the known methods (cf. Swiss Pat. No. 505,773).

b. To a mixture of liquid ammonia (500 ml), tetrahydrofuran (30 ml), tert-butanol (2.796 g) and 3-methyl-5-[2,6,6-trimethyl-cyclohex-1-en-1-yl]-isoxazole (2.593 g; 12.65 millimoles), kept under stirring, there was added sodium metal until the solution acquired a steady blue colour. The reaction mixture was stirred for 15 more minutes, solid ammonium chloride was added thereto until complete discolouration, and the ammonia was then evaporated under a stream of argon. After having added 50 ml of ether and 300 ml of a concentrated ammonium chloride solution in water, the mixture was extracted with two fractions of 300 ml of ether and 150 ml of chloroform, respectively. The combined organic extracts were dried over magnesium sulphate, concentrated under reduced pressure and dissolved in 50 ml of toluene containing traces of p-toluene-sulphonic acid. The thus obtained mixture was refluxed for 24 hours, concentrated in vacuo and then distilled to yield 2.074 g (yield 84%) of 2,6,6-trimethyl-1-[but-2-enoyl]-cyclohex-1-ene; b.p. 55°/0.04 Torr. The analytical data of the obtained product were identical with those of a pure sample prepared by one of the known methods.

EXAMPLE 5

3,4-Dimethyl-5-[2,6,6-trimethyl-cyclohex-2-en-1-yl]-isoxazole

A solution of sodium hydrogenocarbonate (4.50 g) in 25 ml of water was added, while stirring, to a solution of α-isomethyl ionone oxime (2.42 g; 0.011 mole) in 30 ml of tetrahydrofuran.

The process was then carried on in the absence of light, and a solution of potassium iodide (5.80 g) and iodine (2.84 g; 0.011 mole) in 15 ml of water was added. After having been refluxed for 18 hours, the reaction mixture was poured into a concentrated solution of sodium bisulphite (130 ml), extracted with ether (150 ml), and the organic extracts were dried over sodium sulphate and concentrated under reduced pressure. The fractional distillation of the obtained residue yielded 1.380 g of the desired isoxazole (yield 57%): b.p. 72°–74°/0.04 Torr.

IR ($CHCl_3$) : 2910, 1620, 1440, 1414 $cm^{-1}$

NMR ($CDCl_3$) : 0.72 (3H, s); 1.00 (3H, s); 1.50 (3H, m); 1.90 (3H, s); 2.14 (3H, s); 2.96 (1H, broad band, s); 5.63 (1H, m); 1.2 – 2.2 (4H, multiplets) δ ppm UV (95% ethanol): nm max 225 (ε 8150)

MS (70 eV) : $M^+ = 219$.

The α-isomethyl ionone oxime, used as starting material for the preparation of the isoxazole according to the method described above, can be prepared as follows:

16 g of hydroxylamine hydrochloride in 60 ml of water were added to a solution of α-isomethyl ionone (41.2 g; 0.200 mole) in ethanol, kept under vigorous stirring. 22 g of sodium hydrogenocarbonate were then added to the said solution in small portions and the thus obtained mixture was refluxed for 24 hours. After cooling, the said mixture was poured into 250 ml of water, extracted with ether (750 ml) and with methylene chloride (130 ml). The combined organic extracts were dried over magnesium sulphate and concentrated under reduced pressure to give 43.6 g of the desired oxime. There were obtained 41.1 g of α-isomethyl ionone oxime (yield 93%): b.p. 110°–112°/0.05 Torr, by fractional distillation.

IR($CHCl_3$) : 3560, 3250, 2900, 1630 $cm^{-1}$

NMR ($CDCl_3$) : 0.79 (3H, s); 0.92 (3H, s); 1.53 (3H, m); 1.94 (3H, broad band, s); 2.06 (3H, s); 2.66 (1H, d, J = 10 cps); 5.41 (1H, m); 5.69 (1H, d of q, J = 10, 0.5 cps); 9.85 (1H, broad band); 1.2 – 2.2 (4H, multiplets) δ ppm UV (95% ethanol) : nm max 236 (ε 22,800)

MS (70 eV) : $M^+ = 221$.

EXAMPLE 6

2,6,6-Trimethyl-1-[2-methyl-but-2-enoyl]-cyclohex-2-ene

To a mixture of liquid ammonia (500 ml), tetrahydrofuran (160 ml), tert-butanol (18.5 ml) and 3,4-dimethyl-5-[2,6,6-trimethyl-cyclohex-2-en-1-yl]-isoxazole (14.25 g; 0.065 mole), kept under stirring, sodium metal was added until the solution had acquired a steady blue colour. The reaction mixture was further stirred for 20 minutes and solid ammonium chloride was added thereto until complete discolouration, whereupon the ammonia was removed under a stream of argon. After having added 50 ml of ether and 500 ml of a concentrated solution of ammonium chloride in water the mixture was extracted with two fractions of 1500 ml of ether and 100 ml of chloroform, respectively. The combined organic extracts were dried over anhydrous sodium sulphate, concentrated under reduced pressure and the thus obtained residue was dissolved in 350 ml of toluene. The solution in toluene was poured through a Pyrex glass column (13 mm × 150 mm), filled with glass helices previously washed with sulphuric acid and water (3/32 in), heated to 225°–250°.

During the pyrolysis a slow stream of argon was circulated through the apparatus and the product formed was collected in a container cooled by means of dry ice. Concentration under reduced pressure and fractional distillation yielded 7.917 g of 2,6,6-trimethyl-1-[2-methyl-but-2-enoyl]-cyclohex-2-ene (yield 59%): b.p. 70°–71°/0.05 Torr.

IR ($CHCl_3$) : 2920, 1655, 1640 $cm^{-1}$

NMR ($CDCl_3$) : 0.80 (3H, s); 0.97 (3H, s); 1.56 (3H, m); 1.86 (3H, broad band, s); 2.00 (3H, m); 3.54 (1H, broad band, s); 5.63 (1H, m); 6.85 (1H, q, J = 6.5 cps); 1.2 – 2.2 (4H, multiplets) δ ppm UV (95% ethanol): nm max 233 (ε 12,600)

MS (70 eV) : $M^+$ = 206.

EXAMPLE 7

3-Methyl-5-[2-methylene-6,6-dimethyl-cyclohexyl]-isoxazole

A solution of sodium hydrogenocarbonate (13.6 g in 230 ml of water was added to a solution of γ-ionone oxime (8.5 g) in 150 ml of tetrahydrofuran.

The process was then carried on as indicated in Example 1 by adding to the above mentioned solution a solution of potassium iodide (23.5 g) and iodine (10.9 g), whereupon the solution was refluxed for 4 hours. After cooling, the solution was extracted with petroleum-ether. After the usual treatment of drying and evaporation of the volatile portions the combined organic extracts yielded 8.4 g of crude product which, by fractional distillation, gave 6.0 g of the desired isoxazole in the form of a yellowish oil. B.p. 130°/0.001 Torr. The analysis carried out by means of a sample obtained by vapour phase chromatography ("Carbowax" column, 3 m, 180°) showed that the obtained product was constituted by two substances in a ratio by weight of 80:20, the main product being the desired isoxazole. $n_D$ = 1.5025; $d_4^{20}$ = 1.005.

IR : 3080, 1640, 1590, 890 $cm^{-1}$

NMR : 0.92 (6H, 2s); 2.21 (3H, s); 3.3 (1H, s); 4.58 and 4.76 (2H, 2m); 5.75 (1H, s) δ ppm MS : $M^+$ = 205 (23); m/e: 190 (13); 177 (25); 162 (8); 149 (10); 137 (100); 122 (10); 108 (15); 97 (13); 82 (15); 69 (63); 55 (13); 41 (50); 27 (38).

The γ-ionone oxime, used as starting material in the above mentioned preparation, can be prepared as follows:

A solution of 30 g of γ-ionone in 75 ml of ethanol was added to a solution of hydroxylamine hydrochloride (12 g) and sodium acetate (21.6 g) in 30 ml of water. The addition was completed within 5 minutes. The reaction was slightly exothermic, the reaction mixture was stirred for 30 minutes, then it was concentrated under reduced pressure. Thereafter 30 ml of water and 30 ml of ether were added to the said mixture, and it was extracted with petroleum-ether. After drying and concentration, the combined organic extracts yielded a thick oil (31.2 g). An aliquot was distilled in a small distillation tube at a temperature of 180° and a pressure of 0.001 Torr. There was thus obtained a pure product which, as shown by vapour phase chromatography, constituted a mixture of the desired compound in the form of the two syn- and antiisomers in a ratio of 20:80. $n_D$ = 1.5294; $d_4^{20}$ = 0.970.

IR : 3250, 1640, 980, 888 $cm^{-1}$

NMR : 0.85 and 0.92 (6H, 2S); 2.01 (3H, s); 4.54 and 4.72 (2H, 2m); 6.1 (2H, d, J = 5 cps) δ ppm MS : $M^+$ = 207 (0.1); m/e: 191 (1); 176 (3); 159 (2); 148 (1); 136 (3); 123 (4); 107 (3); 91 (2); 81 (3); 69 (3); 58 (20); 43 (100); 27 (38).

EXAMPLE 8

2-Methylene-6,6-dimethyl-1-[but-2-enoyl]-cyclohexane a. 4.1 g of 3-methyl-5-[2-methylene-6,6-dimethyl-cyclohexyl]-isoxazole in 10 ml of anhydrous ethanol were subjected to a hydrogenation in the presence of a small amount of Raney nickel and of KOH. After absorption of 440 ml of hydrogen (corresponding to about 90% of the theoretical amount) the solution was filtered, washed until neutrality and concentrated to yield an oily residue (4 g). By separation by means of vapour phase chromatography ("Carbowax" column, 1.5 m) there was obtained in a yield of 80% 2-methylene-6,6-dimethyl-1-[3-amino-but-2-enoyl]-cyclohexane. $n_D$ = 1.5448; $d^{20}$ = 1.009.

IR : 3400, 1620, 888 $cm^{-1}$

MS : $M^+$ = 207 (3); m/e: 163 (1); 150 (1); 136 (2); 123 (2); 109 (3); 93 (3); 84 (100); 69 (8); 55 (3); 41 (9); 29 (2).

To a mixture of liquid ammonia (about 200 ml), tert-butanol (2.8 g) and 2.1 g of 2-methylene-6,6-dimethyl-1-[3-amino-but-2-enoyl]-cyclohexane there were added 1.5 g of sodium metal. The solution showed a steady blue colour. The reaction mixture was stirred for 15 more minutes and the procedure of Example 2 repeated. By extraction with chloroform and concentration of the organic extracts there was obtained a residue which, after extraction by means of a mixture of ether and chloroform in a ratio by weight of 2:1 followed by the usual treatments of drying and evaporation, yielded 3 g of an oily product consisting of 2-methylene-6,6-dimethyl-1-[3-amino-butanoyl]-cyclohexane.

IR : 3200, 1710, 1635, 890 $cm^{-1}$

NMR : 0.86 and 0.96 (6H, 2s); 1.12 (3H, d, J = 6 cps); 2.95 (1H, s); 4.7 and 4.8 (2H, 2m) δ ppm MS : $M^+$ = 209 (0.2); m/e: 192 (8); 177 (7); 166 (3); 149 (7); 137 (12); 123 (20); 109 (37); 93 (15); 81 (30); 69 (90); 57 (35); 41 (58); 27 (15).

By following the above indicated procedure it is possible to prepare also the desired amino derivative by direct reduction of 3-methyl-5-[2-methylene-6,6-dimethyl-cyclohexyl]-isoxazole by means of sodium metal.

b. 1 g of 2-methylene-6,6-dimethyl-1-[3-amino-butanoyl]-cyclohexane in 25 ml of toluene was refluxed for 3 hours in the presence of a catalytic amount of p-toluene-sulphonic acid. The obtained solution was wahsed with a 10% solution of sodium hydrogenocarbonate in water until neutrality, then dried and concentrated. 0.6 g of 2-methylene-6,6-dimethyl-1-[but-2-enoyl]-cyclohexane was thus obtained. The analytical data were in agreement with those of a pure sample prepared by one of the known methods.

EXAMPLE 9

A basic perfume composition was prepared by admixing the following ingredients (parts by weight):

| Ingredient | Parts |
|---|---|
| Menthol | 10 |
| Eugenol | 50 |
| Coumarin | 20 |
| 10 % Muskone * | 20 |
| Phenylethyl alcohol | 120 |
| Lavender | 210 |
| Pimento oil | 40 |
| Cinnamon oil | 5 |
| Synthetic bergamot | 270 |
| 10 % Cyclopentadecanone * | 30 |
| Methyl dihydrojasmonate | 20 |
| Oak moss absolute | 15 |
| Benzyl salicylate | 20 |
| Isobutyl salicylate | 30 |
| Geranium Bourbon oil | 70 |
| Musk ketone | 20 |
| Total | 950 |

* in 95 % ethanol

By adding to 9.5 parts of the above indicated composition 0.5 parts of 3-methyl-5-[2,6,6-trimethyl-cyclohex-2-en-1-yl]-isoxazole, a composition having a particularly harmonious note of oriental tobacco is obtained. Analogous effects were observed by the addition to the basic composition of 3-methyl-5-[2,6,6-trimethyl-cyclohex-1-en-1-yl]-isoxazole or 3-methyl-5-[2-methylene-6,6-dimethyl-cyclohexyl]-isoxazole. A particularly interesting effect was observed when using 3,4-dimethyl-5-[2,6,6-trimethyl-cyclohex-2-en-1-yl]-isoxazole, as the tobacco note was particularly powerful in this case.

EXAMPLE 10

Preparation of a flavouring composition of the "Tutti-Frutti' type

A flavouring composition of the "Tutti-Frutti" type was prepared by admixing the following ingredients (parts by weight):

| Ingredient | Parts |
|---|---|
| Vanillin | 20 |
| Allyl caproate | 10 |
| Citral | 20 |
| Amyl butyrate | 35 |
| Orange oil | 45 |
| Ethyl butyrate | 75 |
| Ethyl acetate | 185 |
| Amyl acetate | 185 |
| Lemon oil | 400 |
| Total | 975 |

25 g of 3-methyl-5-[2,6,6-trimethyl-cyclohex-2-en-1-yl]-isoxazole were added to 975 g of the above mixture referred to as "Test" composition. A "Check" composition was prepared by the addition of 25 g of lemon oil to 975 g of the above mixture.

The "Test" and the "Check" compositions were added to the foodstuffs described below at the indicated concentrations (per 100 kg of product to be flavoured):

| | |
|---|---|
| Cake | 20 g |
| Custard | 5 – 10 g |
| Caramel | 15 – 20 g |

Caramel: 100 ml of sugar syrup (obtained by dissolving 1 kg of sucrose in 600 ml of water) and 20 g of glucose were mixed and slowly heated to 145°. The flavour was added to the mass and the mixture was allowed to cool and to harden.

Custard: 60 g of sucrose and 3 g of pectin were added, with stirring, to 500 ml of warm milk. The mixture was heated to the boil for a few seconds and the flavour was added, whereupon the whole mixture was cooled.

Cake: the following ingredients were mixed: 100 g of vegetable margarine, 1.5 g of NaCl, 100 g of sucrose, 2 eggs and 100 g of flour. The flavour was added to the above mass and the whole was heated to 180° for 40 minutes. Samples of the finished foodstuff were tasted by a group of experts who had to express their opinion as to the taste of the samples submitted to them. All the members of the group declared without hesitation that the "Test" samples had a more marked fruity note than that of the "Check" samples.

EXAMPLE 11

3-Methyl-5-[2,6,6-trimethyl-cyclohex-1-en-1-yl]-N-methyl-isoxazolium iodide 5.0 ml of methyl iodide and 0.270 g (1.31 mole) of 3-methyl-6-[2,6,6-trimethyl-cyclohex-1-en-1-yl]-isoxazole, which can be prepared according to the procedure indicated in Example 3, were heated overnight in a sealed tube to about 100°. After cooling and evaporation of the excess methyl iodide there was obtained a crystalline product which after recrystallization from a mixture of chloroform/carbon tetrachloride and acetone yielded 0.230 g (yield 50%) of the desired isoxazolium salt. M.p. 208°–209°.

IR ($CHCl_3$) : 1595, 1520 $cm^{-1}$

NMR ($CDCl_3$) : 1.07 (6H, s); 1.4 – 2.3 (6H; multiplets); 1.73 (3H, s); 3.03 (3H, s); 4.54 (3H, s); 6.89 (1H, s) $\delta$ ppm UV max (95% ethanol) : 221 ($\epsilon = 21,500$); 275 ($\epsilon = 4,860$) nm When 3-methyl-5-[2,6,6-trimethyl-cyclohex-2-en-1-yl]-isoxazole, which can be prepared according to the process described in Example 1, is subjected to the same treatment, the same isoxazolium salt as that obtained from the cyclohex-1-ene derivative is obtained with a yield of 41%.

EXAMPLE 12

3-Methyl-5-[2,6,6-trimethyl-cyclohex-2-en-1-yl]-isoxazole 54 g of 4-[2,6,6-trimethyl-cyclohex-2-en-1-yl]-3,4-epoxy-2-butanone-oxime, which can be prepared as indicated above, in 500 ml of benzene were refluxed in the presence of 2 g of p-toluenesulphonic acid for about 4 hours. The water formed in the course of the reaction was removed as it formed by azeotropic distillation.

The reaction mixture was then washed with an $NaHCO_3$ solution until it was neutral, dried over anhydrous $Na_2SO_4$ and distilled. There were thus obtained 35 g (71%) of a product, b.p. 73°–74°/0.01 Torr. The analytical data were identical with those indicated in Example 1.

The butanone-oxime used as starting product in the above process can be prepared as follows:

50 g of $\alpha,\beta$-epoxy-$\alpha$-ionone [which can be synthesized according to the method indicated in Helv. Chim. Acta, 53, 531 (1970)] in 140 ml of ethanol were slowly added to a solution of sodium acetate (35 g) in 50 ml of warm water and 20 g of hydroxylamine hydrochloride.

The reaction mixture was stirred overnight, the volatile portions were removed under reduced pressure and the thus obtained residue diluted with 100 ml of water. Extraction with petroleum-ether, separation, washing, drying and concentration of the organic extracts yielded 53.6 g of a viscous oil which, after distillation, gave a product of b.p. 120°–130°/0.1 Torr;

$n_D$ = 1.5101; $d^{20}$ = 1.012.

IR : 3250 $cm^{-1}$

NMR : 0.94 and 1.1 (6H, 2s); 1.68 (3H, s); 1.7 (3H, s); 2.75 and 3.32 (2H); 5.45 (1H, m) δ ppm MS : $M^+$ = 223 (0.1); m/e: 205 (8); 192 (2); 177 (2); 149 (34); 137 (34); 123 (83); 109 (46); 93 (34); 81 (80); 67 (36); 55 (34); 43 (100); 27 (40).

EXAMPLE 13

3-Methyl-5-[2-methylene-6,6-dimethyl-1-cyclohexyl]-isoxazole 2.1 g of threo-4-[2-methylene-6,6-dimethyl-1-cyclohexyl]-3,4-epoxy-2-butanone-oxime which can be prepared from epoxy-γ-ionone [Helv. Chim. Acta, 54, 1805 (1971)] were treated as indicated in Example 12. There were thus obtained 1.4 g of the desired isoxazole. B.p. 70°–73°/0.01 Torr. The analytical data were identical with those shown by a pure sample prepared according to the process indicated in Example 7.

By treating the erythro-drivative according to the conditions indicated above the desired isoxazole is also obtained.

The threo- and erythro-butanone-oximes used as starting materials in the above process can be prepared as follows:

2 g of epoxy-γ-ionone (threo; $n_D$ = 1.4890; $d^{20}$ = 0.9972) prepared as indicated in Helv. Chim. Acta, 54, 1805 (1971) were converted into the corresponding oxime according to the method given in Example 12 by treatment with 0.8 g of hydroxylamine hydrochloride and 1.6 g of sodium acetate in 2 ml of water and 5 ml of ethanol.

In the same manner the conversion of the erythro-epoxy-γ-ionone (m.p. 43°) was effected to obtain the corresponding butanone-oxime.

We claim:

1. A process for preparing compounds of formula

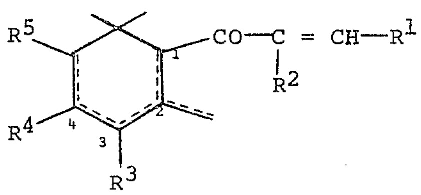

IV wherein the ring contains one endocyclic double bond in position 1, 2, 3 or 4, or an exocyclic double bond in position 2, or two conjugated double bonds in position 1 and 3, the double bonds being represented by dotted lines; and each of the symbols $R^1$, $R^2$, $R^3$, $R^4$ and $R^5$ represents either a hydrogen atom or a lower alkyl radical having 1 to 6 carbon atoms; which comprises:

a. reducing a compound having the formula

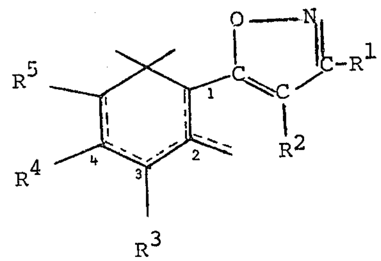

I wherein the dotted lines and the symbols $R^1$, $R^2$, $R^3$, $R^4$ and $R^5$ are as described above, by means of an alkali metal or an alkaline earth metal in solution of liquid ammonia and in the presence of tert-butanol as a proton donor to yield a β-amino-ketone compound having the formula

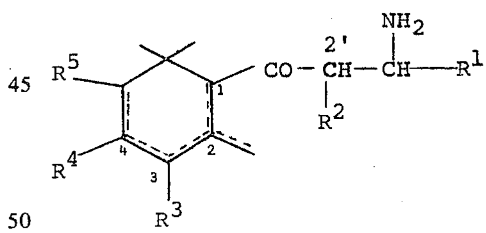

V wherein the dotted lines of the ring and the symbols $R^1$, $R^2$, $R^3$, $R^4$ and $R^5$ are as described above; and b. subsequently removing an ammonia molecule from the said β-amino-ketone compound by addition of a mineral acid or p-toluene-sulphonic or by heating.

2. A process for preparing compounds of formula

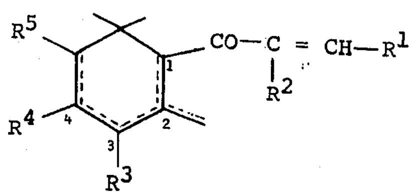

(IV)

wherein the ring contains one endocyclic double bond in position 1, 2, 3 or 4, or an exocyclic double bond in position 2, or two conjugated double bonds in position 1 and 3, the double bonds being represented by dotted lines; and each of the symbols $R^1$, $R^2$, $R^3$, $R^4$ and $R^5$ represents either a hydrogen atom or a lower alkyl radical having 1 to 6 carbon atoms; which comprises a. reducing a compound having the formula

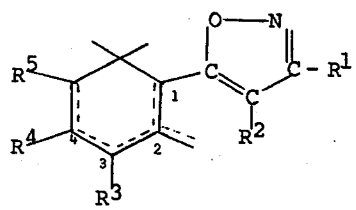

wherein the dotted lines and the symbols $R^1$, $R^2$, $R^3$, $R^4$ and $R^5$ are as described above, by means of catalytic hydrogenation to yield a β-imino-ketone equilibrium reaction mixture of

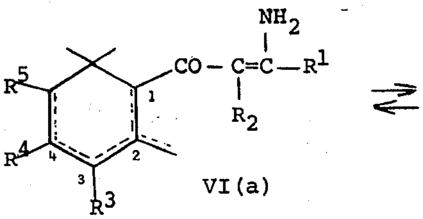

⇄

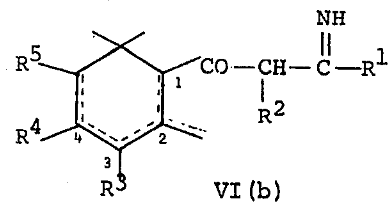

wherein the dotted lines and the symbols $R^1$, $R^2$, $R^3$, $R^4$ and $R^5$ are as described above; and b. subsequently further adding to the reaction mixture of a. a reducing agent selected from the group of 1. an alkali metal or alkaline earth metal in solution of liquid ammonia and in the presence of tert-butanol as a proton donor; and
2. sodium cyanohydroborate to yield a β-amino ketone compound having the formula

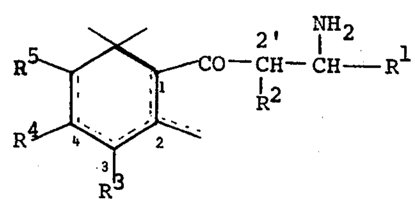

V wherein the dotted lines and the symbols $R^1$, $R^2$, $R^3$, $R^4$ and $R^5$ are as described above; and c. subsequently removing an ammonia molecule from the said β-amino-ketone compound by addition of a mineral acid or p-toluene-sulphonic acid or by heating.

* * * * *

UNITED STATES PATENT AND TRADEMARK OFFICE

CERTIFICATE OF CORRECTION

PATENT NO. : 3,931,323

DATED : January 6, 1976

INVENTOR(S) : GEORGE HERMANN BUCHI ET AL.

It is certified that error appears in the above-identified patent and that said Letters Patent are hereby corrected as shown below:

Column 7, line 46 "$X^-$, $I^-$, $Br^-$, $Cl^-$, $BF_4^-$, or $ClO_4^-$" should read -- $X^{\ominus}$, $I^{\ominus}$, $Br^{\ominus}$, $Cl^{\ominus}$, $BF_4^{\ominus}$, or $ClO_4^{\ominus}$ --.

Column 9, line 21 "ann" should read -- an --.

Column 16, line 9 "(6H, 25)" should read -- (6H, 2s) --.

Column 16, line 65 "wahsed" should read -- washed --.

Column 17, line 38 " "Tutti-Frutti' " should read -- "Tutti-Frutti" --.

In the Claims

Claim 1b, column 20, line 66 "p-toluene-sulphonic" should read -- p-toluene-sulphonic acid --.

Signed and Sealed this

*fourth* Day of *May 1976*

[SEAL]

*Attest:*

RUTH C. MASON
*Attesting Officer*

C. MARSHALL DANN
*Commissioner of Patents and Trademarks*